United States Patent
Bourne et al.

(10) Patent No.: US 6,960,208 B2
(45) Date of Patent: Nov. 1, 2005

(54) APPARATUS AND METHODS FOR DELIVERING ENERGY TO A TARGET SITE WITHIN BONE

(75) Inventors: George Bourne, Southborough, MA (US); Robert Rioux, Ashland, MA (US); Robert Garabedian, Tyngsboro, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 144 days.

(21) Appl. No.: 10/611,222

(22) Filed: Jun. 30, 2003

(65) Prior Publication Data

US 2004/0267257 A1 Dec. 30, 2004

(51) Int. Cl.[7] .................................................. A61B 18/18
(52) U.S. Cl. ........................................... 606/41; 606/45
(58) Field of Search ........................... 607/96–103, 115; 606/27–52, 79–80, 96, 98

(56) References Cited

U.S. PATENT DOCUMENTS

| | | | |
|---|---|---|---|
| 4,632,100 A | | 12/1986 | Goble et al. |
| 5,554,154 A | * | 9/1996 | Rosenberg ................... 606/80 |
| 5,611,515 A | | 3/1997 | Benderev et al. |
| 5,941,876 A | | 8/1999 | Nardella et al. |
| 5,989,278 A | | 11/1999 | Mueller |
| 6,156,031 A | | 12/2000 | Aita et al. |
| 6,162,214 A | | 12/2000 | Mueller et al. |
| 6,190,383 B1 | * | 2/2001 | Schmaltz et al. ............. 606/41 |
| 6,315,774 B1 | | 11/2001 | Daniel et al. |
| 6,478,793 B1 | * | 11/2002 | Cosman et al. ............... 606/34 |
| 6,540,747 B1 | * | 4/2003 | Marino ......................... 606/61 |
| 6,622,731 B2 | * | 9/2003 | Daniel et al. ................ 128/898 |
| 2004/0087958 A1 | * | 5/2004 | Myers et al. .................. 606/80 |

FOREIGN PATENT DOCUMENTS

| | | |
|---|---|---|
| DE | 43 12 147 | 10/1993 |
| DE | 198 26 079 | 3/2000 |
| WO | WO 97/33523 | 9/1997 |
| WO | WO 01/32088 A2 | 5/2001 |

OTHER PUBLICATIONS

PCT International Search Report for PCT/US2004/013288, Applicant: Scimed Life Systems, Inc., Forms PCT/ISA/210 and 220, dated Sep. 8, 2004 (5 pages).
PCT Written Opinion of the International Search Authority for PCT/US2004/013288, Applicant: Scimed Life Systems, Inc., Form PCT/ISA/237, dated Sep. 8, 2004 (7 pages).

* cited by examiner

*Primary Examiner*—Michael Peffley
(74) *Attorney, Agent, or Firm*—Bingham McCutchen LLP

(57) ABSTRACT

An apparatus for delivering energy to a target site within bone includes a hollow needle extending from a handle that terminates in a tissue piercing distal tip. A drill within a lumen of the needle is extendable beyond the distal tip, and includes a cutting element and an electrically conductive region. An RF generator may be coupled to the drill for delivering energy to the electrically conductive region, and a driver or actuator may be coupled to the drill for rotating and/or advancing the drill axially. During use, the needle is inserted through a patient's skin to a hard tissue structure, e.g., a bone, including a target site therein, e.g., a tumor. The drill is advanced from the needle, a hole is drilled into the bone until the drill reaches the tumor, and electrical energy is delivered via the electrically conductive region to destroy the tumor.

39 Claims, 5 Drawing Sheets

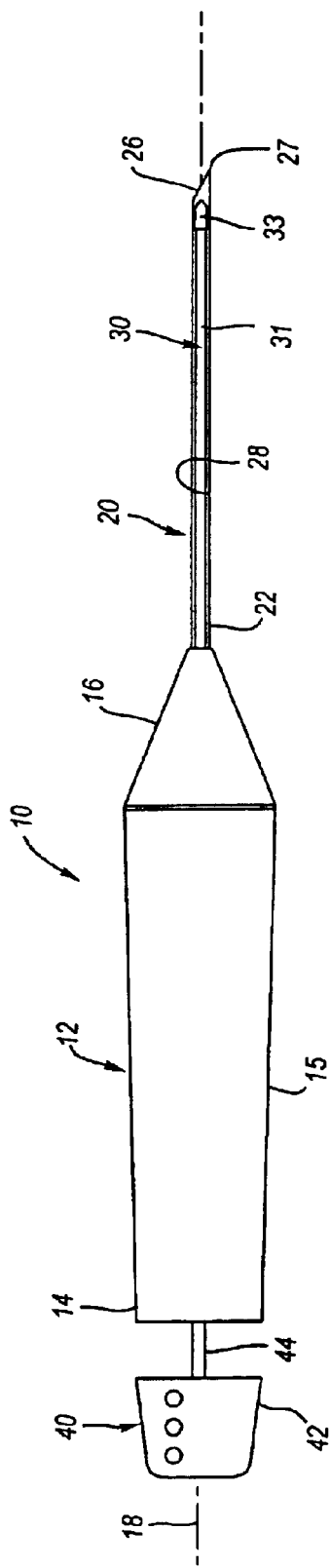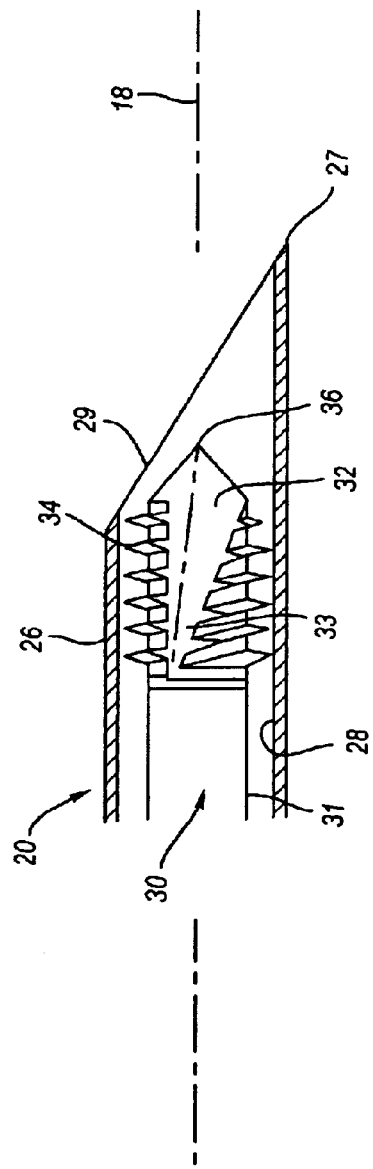
FIG. 1A
FIG. 2A

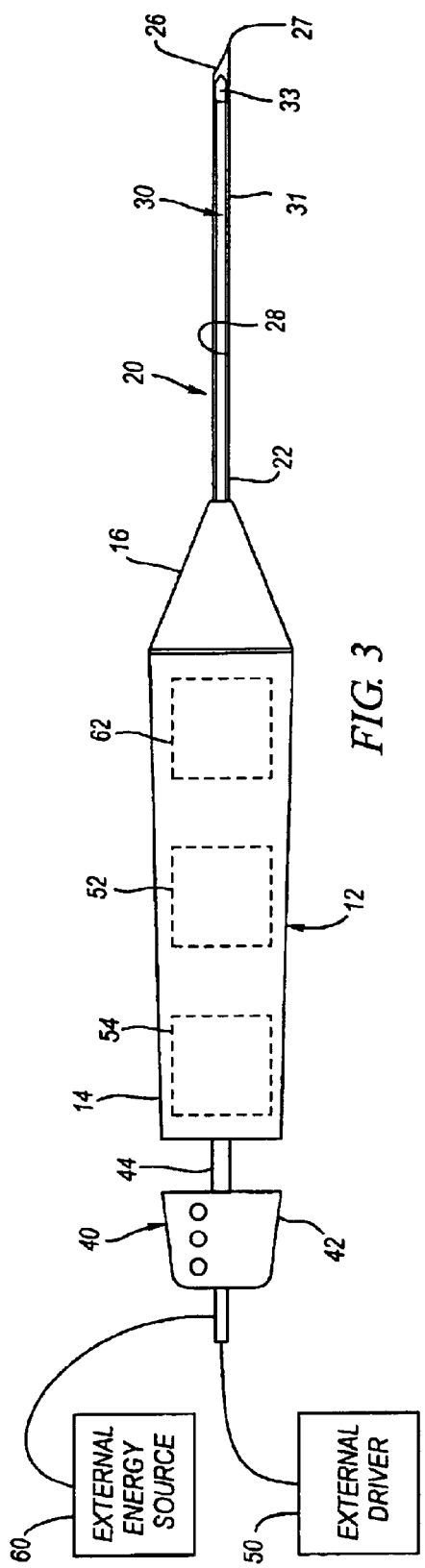
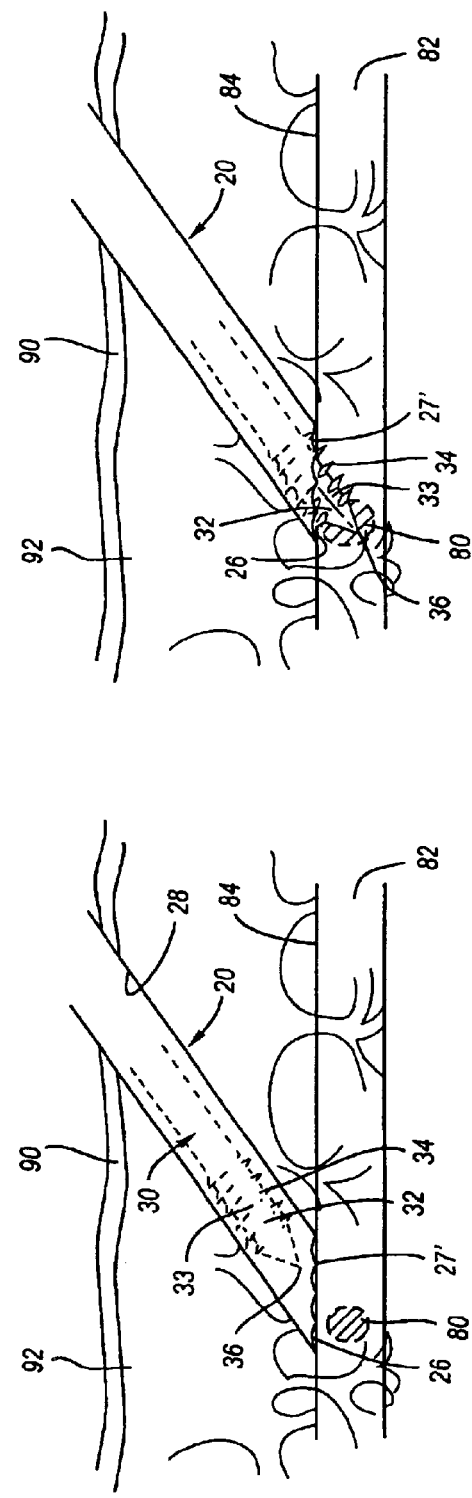
FIG. 3
FIG. 4A
FIG. 4B

APPARATUS AND METHODS FOR DELIVERING ENERGY TO A TARGET SITE WITHIN BONE

FIELD OF THE INVENTION

The present invention relates generally to apparatus and methods for delivering energy to a region within a patient's body, and, more particularly, to apparatus and methods for percutaneously delivering therapeutic energy, for example, radio frequency ("RF") electrical energy, to a target region within a hard tissue structure, such as bone.

BACKGROUND

It is well know to ablate or otherwise treat tissue, such as a benign or malignant tumor by heating the tumor with energy, such as electrical energy. To accomplish this, a probe may be inserted into a target region impacted by tumor, and energy may be delivered from the probe to the tissue within the target region. For example, to treat Osteoid Osteomas, a benign bone-forming tumor that most commonly affects children and young adults, a probe, e.g., an RF energy probe including an electrically conductive region, may be used to deliver energy to ablate the Osteoid Osteomas.

Before inserting the probe into bone, a pilot hole must be created in the bone using a drill or other bone access tool. Once the pilot hole is created, the drill or access tool is removed, and the probe is inserted into the pilot hole to ablate the Osteoid Osteomas. Alternatively, open surgery may be used to expose the target bone before inserting the probe. Open surgery, however, has several disadvantage, such as increased morbidity, and extended recovery.

Accordingly, apparatus and methods for delivering energy to a target region within a patient's body would be useful.

SUMMARY OF THE INVENTION

The present invention is directed to apparatus and methods for delivering energy to a target region within a patient's body, and, more particularly, to apparatus and methods for percutaneously delivering therapeutic energy, for example, radio frequency ("RF") electrical energy, to a target region within a hard tissue structure, such as bone.

In accordance with one aspect of the present invention, an apparatus is provided for delivering energy to a target site within a patient that includes a handle and an elongated needle extending from the handle. The needle may be substantially rigid and/or may terminate in a tissue piercing distal tip, e.g., a beveled and/or serrated tip, and may include a lumen therein extending from the distal tip towards the handle.

A drill is disposed within the lumen that is extendable from the distal tip of the needle. The drill may include a cutting element for boring a hole in a hard tissue structure, e.g., a helical thread pattern extending along a bit or head of the drill, which may be substantially permanently attached to or selectively detachable from the drill. The thread pattern may include one or more helical threads, which may be continuous or discontinuous. The drill may also include an element for delivering energy, e.g., an electrode or other electrically conductive region on the bit or head. An energy source, e.g., an RF generator, may be coupled to the drill for delivering energy to the electrically conductive region.

A driver may be coupled to the drill for rotating the drill about a longitudinal axis of the needle, e.g., an electric or pneumatic motor located inside or external to the handle or a manual mechanical drive. The driver may also be configured for advancing the drill axially, e.g., as the drill is rotated. Alternatively, an actuator may be provided on the handle that is coupled to the drill such that axial movement of the drill relative to the distal tip of the needle is controllable by manipulating the actuator. Optionally, the actuator may include a lock for selectively preventing the drill from moving axially relative to the distal tip of the needle.

In accordance with another aspect of the present invention, a method is provided for treating a target site within a hard tissue structure. A needle may be advanced through tissue, e.g., through a patient's skin and any intervening tissue, to a hard tissue structure, such as a bone, including a target site therein, such as a tumor. The tip of the needle may be at least partially penetrated into a surface of the hard tissue structure to prevent substantial lateral movement of the needle relative to the hard tissue structure.

A drill may be extended from the needle, and a hole drilled into the hard tissue structure with the drill to access the target site. Energy, e.g., RF electrical energy, may be delivered to the target site via the drill, for example, from an electrically conductive region on the drill, to destroy or otherwise treat the tumor. The drill may be withdrawn from the target site, or at least a portion of the drill, e.g., a bit, may be implanted at the target site, e.g., by detaching the bit from the drill during or after treating tissue at the target site.

Other objects and features of the present invention will become apparent from consideration of the following description taken in conjunction with the accompanying drawings.

BRIEF DESCRIPTION OF THE DRAWINGS

FIGS. 1A and 1B are side views of a preferred embodiment of an apparatus for treating tissue within a hard tissue structure, including a drill retracted into and deployed from a needle, respectively, in accordance with the present invention.

FIGS. 2A and 2B are details of a distal end of the needle of FIGS. 1A and 1B, respectively.

FIG. 3 is a side view of an alternative embodiment of an apparatus for treating tissue within a hard tissue structure, in accordance with the present invention.

FIGS. 4A and 4B are cross-sectional views of a tissue structure, showing a method for treating a tumor within the tissue structure, in accordance with the present invention.

DETAILED DESCRIPTION OF THE INVENTION

Figure 1B:
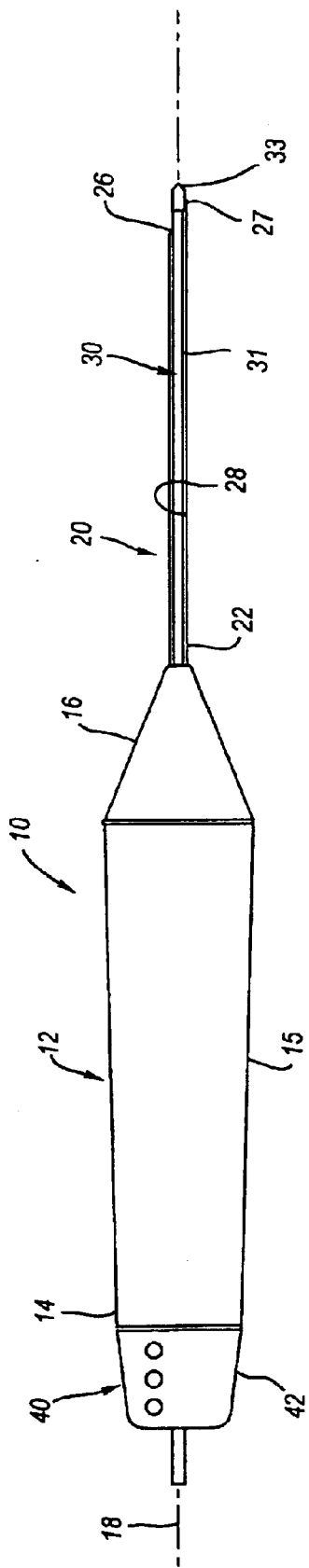

Turning to the drawings, FIGS. 1A–2B show a preferred embodiment of an apparatus 10 for ablating or otherwise treating tissue within a hard tissue structure. As best seen in FIGS. 1A and 1B, the apparatus 10 generally includes a handle 12, a needle 20 extending from the handle 12, and a drill 30 that may be advanced from the needle 20. The handle 12 includes a proximal end 14 with an actuator 40 thereon and a distal end 16 from which the needle 20 extends.

The needle 20 includes a proximal end 22 coupled to the distal end 16 of the handle 12 and a distal end 26 that terminates in a tissue piercing distal tip 27, thereby defining a longitudinal axis 18. The needle 20 is a hollow tubular member including a lumen 28 that extends from the proximal end 22 to an opening 29 in the distal end 26. The needle 20 may be formed from biocompatible material, such as stainless steel, plastic, and the like. If the needle 20 is formed from an electrically conductive material, e.g., stainless steel, an inner and/or outer surface of the needle 20 may be electrically insulated, e.g. by coating the surface(s), and/or covering the surface(s) with a layer of plastic or other non conductive material.

Preferably, the needle 20 is substantially rigid and straight, although alternatively, the needle 20 may be semi-rigid, curved, and/or malleable. For example, in an alternative embodiment, the needle may include one or more bends (not shown), such as the two-bend needle 120 shown in FIG. 5 and described further below.

The distal tip 27 of the needle 20 may be substantially smooth and sharp, e.g., beveled, as shown, or otherwise pointed. Optionally, the needle may include a serrated tip 27,' such as that shown in FIGS. 4A and 4B. The distal tip 27 may include any shape, sharpness, angle, and/or number of serrations sufficient to pierce tissue and/or to engage a surface of a hard tissue structure. For example, with the serrated tip 27' or beveled tip 27, the distal end 26 of the needle 20 may at least partially penetrate or otherwise engage the surface of a hard tissue structure to prevent substantial movement of the apparatus 10 during a procedure, as described further below.

Figure 6A:
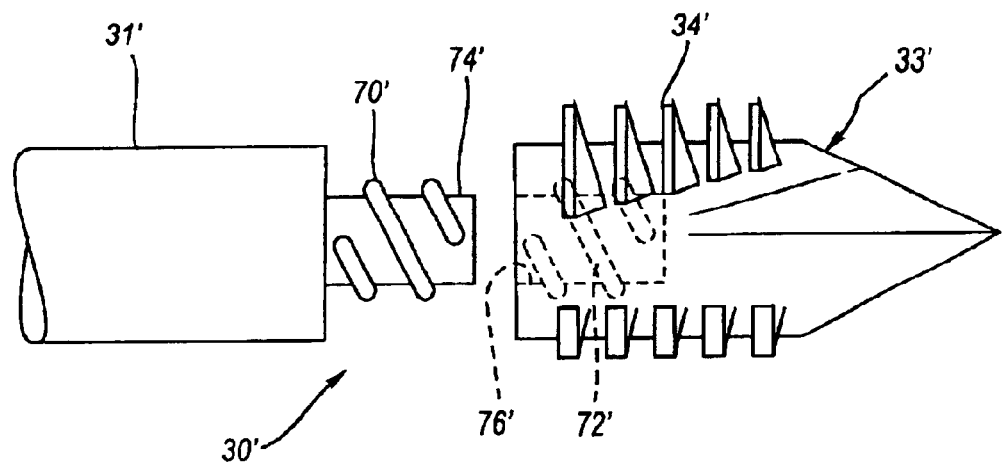
FIGS. 6A and 6B are details showing alternative embodiments of a drill including a detachable bit that may be incorporated into the apparatus of FIG. 1.
Figure 6B:
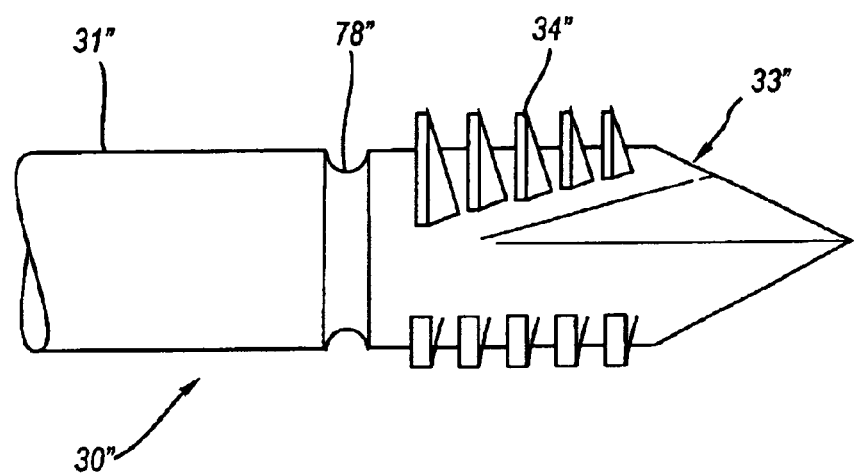

The drill 30 includes an elongate shaft 31 that extends through the lumen 28 of the needle 20 from the handle 12 and terminates in a drill head or bit 33. The drill 30 may be formed as a single piece, or as multiple parts that may be coupled to one another such that rotation and/or axial movement of one part translates substantially to adjacent part(s). The bit 33 may be substantially permanently attached to the shaft 31, or alternatively, as shown in FIGS. 6A and 6B, and described further below, a bit 33' or 33" may be provided that is detachable from the shaft 31' or 31," e.g., such that the bit may be released from the shaft during or after a procedure.

Figure 2B:
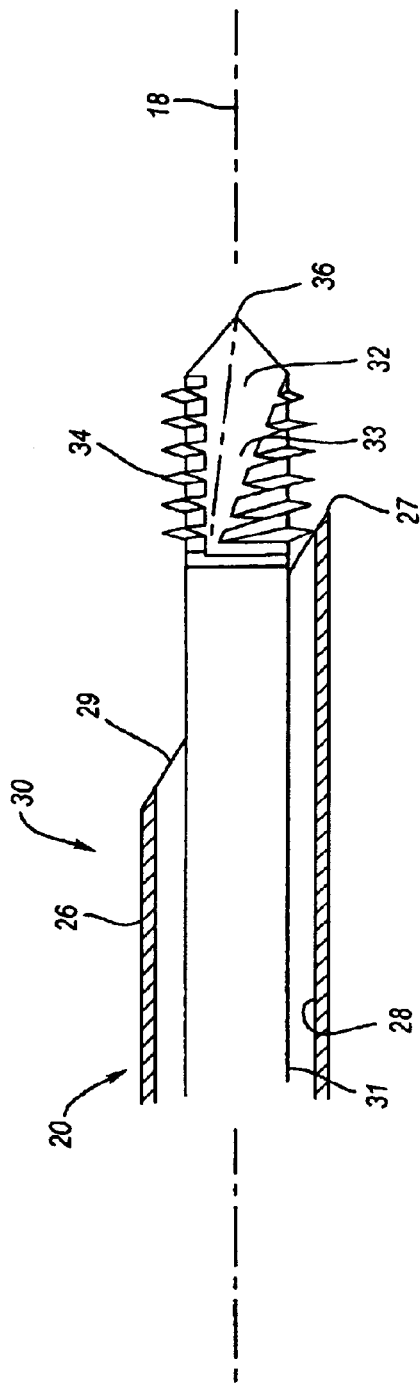

The bit 33 may include an electrically conductive region 32 (best seen in FIGS. 2A and 2B). For example, one or more electrodes (not shown) may be formed on the bit 33, e.g., by vapor deposition, bonding, press-fit, and the like. Alternatively, all or a desired region of the bit 33 or the entire drill 30 may be formed from an electrically conductive material, e.g., copper, aluminum, or stainless steel. If the shaft 31 is not electrically conductive, a conductor, e.g., one or more wires (not shown), may extend from the bit 33 along the inner or outer surface of the shaft 31 and into the handle 12, e.g., coupled to the electrically conductive region 32.

The bit 33 also includes a cutting element for boring into a hard tissue structure, e.g., a bone (not shown), to create a tract or hole therein. For example, the bit 33 may include a thread pattern 34 extending about the longitudinal axis 18. The thread pattern 34 may include one or more helical threads or flutes, which may be discontinuous (as shown in FIGS. 2A and 2B) or may extend continuously around the outer surface of the bit 33 (not shown). As is well known to those skilled in the art, such threaded or helical features may facilitate penetrating and/or boring the bit 33 into a tissue structure having a hard surface, such as bone. In addition, the bit 33 may include a pointed tip 36 to penetrate initially into a surface of a hard tissue structure to facilitate engaging the thread pattern 34 with the tissue structure.

In the embodiment shown, the needle 20 and drill 30 are substantially permanently attached to the handle 12. Alternatively, one or both of the needle 20 and the drill 30 may be detachable from the handle 12. For example, coaxial hubs or shafts (not shown) may extend from the handle 12 that terminate in connectors (also not shown). Separate needle and/or drill components (also not shown) may include mating connectors such that they may be coupled to the respective hubs or shafts. Thus, the needle 20 and/or drill 30 may be used during a single procedure and then disposed of, while the handle 12 may be reused, e.g., after being sterilized. In addition, detachable needle and drill components may accommodate providing a kit including a variety of needles and drills, e.g., having different lengths, sizes, and/or tip configurations, that may be selected based upon the anatomy encountered during a particular procedure. The components may include separate needles and drills or may include matching sets of needles and drills.

An actuator 40 may be provided on the handle 12 that may be coupled to the drill 30 such that the bit 33 may be advanced, retracted, and/or rotated by manipulating the actuator 40. For example, as shown in FIG. 1A, the actuator 40 may include a knob 42 coupled to a stem 44, which may, in turn, be coupled to a proximal end (not shown) of the shaft 31 of the drill 30. The knob 42 may be pulled proximally, i.e., away from the handle 12, so that the bit 33 of the drill 30 is withdrawn into the lumen 28 of the needle 20, as shown in FIG. 2A. As shown in FIG. 1B, the actuator 40 may be pushed distally, i.e., towards the handle 12, such that the bit 33 of the drill 30 extends out of the lumen 28, as shown in FIG. 2B. The actuator 40 may include a lock or stop (not shown) that prevents or otherwise limits advancing or retracting the drill 30 relative to the needle 20. For example, once the bit 33 is advanced, a lock may be engaged to prevent the bit 33 from accidentally retracting back into the needle 20.

Optionally, besides allowing axial movement of the drill 30, the actuator 40 may be rotated about the longitudinal axis 18, e.g., by manually rotating the knob 42, to rotate the bit 33 of the drill 30. This rotation may be independent from any axial movement e.g., whether the bit 33 is advanced or withdrawn, and/or the drill 30 may be rotated and advanced simultaneously. Alternatively, the handle 12 and knob 42 may be replaced with a squeeze handle 112, such as that shown in FIG. 5. The handle 112 may include a stationary handle grip 113 and a trigger 140 that may be pulled to rotate the drill 130 relative to the needle 120. The handle 12 may include an internal mechanical drive (not shown) that translates linear movement of the trigger 140 into rotational movement of the drill 130, as explained further below with respect to FIG. 5. In addition, the trigger 140 may advance the bit 33 from the distal tip 27 of the needle 20 as the trigger 140 pulled, e.g., before or simultaneous with rotating the drill 130. In a further alternative, the inner surface of the needle and the outer surface of the drill may include cooperating elements, such as one or more tabs slidably received in helical slots (not shown) that cause the bit 33 to advance or retract at a predetermined rate as the drill 30 is rotated.

Turning to FIG. 3, in addition or alternatively, an external driver 50 may be coupled to the shaft 31 of the drill 30 for rotating the drill 30 about the longitudinal axis 18. The driver 50 may be bidirectional, i.e., may rotate clockwise as well as counterclockwise, e.g., to rotate the drill 30 in a direction to advance the bit 33 into the tissue and/or to withdraw the bit 33 from tissue, as explained further below.

Optionally, the driver 50 may rotate the drill 30 while also providing an axial force to advance or withdraw the bit 33. Alternatively, an internal motor or driver 52 (shown in phantom) may be provided, e.g., inside the handle 12 or the actuator 40. In this alternative, the handle 12 may include a battery 54 (also shown in phantom), which may allow the apparatus 10 to be operated without being connected to an external power source. In a further alternative, the handle 12 may include one or more cables and/or connectors for coupling the internal driver 52 to an energy source (not shown). Although an electrical energy source may be preferred, other energy sources and/or drivers, e.g., pneumatic or other fluid-driven systems, may be used to rotate and/or advance the drill 30, as will be appreciated by those skilled in the art.

An energy source, e.g., a radio frequency (RF) generator 60, may be coupled via the actuator 40, the handle 12, or otherwise to the drill 30 for delivering energy to the electrically conductive region 32 of the bit 33. For example, as described above, the shaft 31 of the drill 30 may be formed from an electrically conductive material, or may include a conductor, e.g., one or more wires (not shown), that extends to the electrically conductive region 32. Thus, the electrically conductive region 32 may be coupled to the energy source 60, e.g., via the shaft 31, the handle 12, and/or wires or cables (not shown). Alternatively, it may be possible to provide other elements on the bit 33 of the drill 30 for heating and/or otherwise destroying tissue, e.g., using microwave, ultrasound, laser, ultra-violet, and/or cryogenic energy.

Optionally, the apparatus 10 may include one or more sensors (not shown) for monitoring a parameter during use. For example, a thermocouple, thermister, or other temperature sensor (not shown) may be provided on the bit 33 in or adjacent to the electrically conductive region 32 and/or on the distal end 26 of the needle 20. The sensor(s) may be coupled to a processor within or separate from the RF generator 60 or other energy source. Preferably, one or more temperature sensors are provided for monitoring the temperature of tissue surrounding the bit 33 during use, e.g., to prevent overheating that might char or otherwise damage healthy tissue, as explained further below.

Turning to FIGS. 4A and 4B, the apparatus 10 may be used to treat a target tissue region 80 percutaneously, e.g., an Osteoid Osteomas or other benign or malignant tumor, within a hard tissue structure, such as bone 82. Initially, the target region 80 may be detected and/or identified using any known method, such as computer tomography ("CT") and/or X-ray. The apparatus 10 may be prepared such that the bit 33 of the drill 30 is positioned completely inside the lumen 28 of the needle 20 (as shown in FIGS. 1A and 2A). If the handle 12 and/or actuator 40 includes a lock (not shown), the drill 30 may be locked to prevent the bit 33 from inadvertently advancing from the needle 20 prematurely. In addition, if the apparatus is modular (not shown), an appropriate needle and/or drill configuration may be selected and attached to the handle 12 once the target region 80 is identified and located.

Turning to FIG. 4A, the needle 20 may be inserted into the patient, e.g., by penetrating the patient's skin 90 with the distal tip 27' and advancing the needle 20 through any intervening tissue 92, until the distal end 26 of the needle 20 reaches a surface 84 of the bone 82. As shown in FIG. 4A, the distal end 26 of the needle 20 may include a serrated tip 27' that may penetrate partially into or otherwise substantially engage the surface 84 of the bone 82. Serrations on the serrated tip 27' may be forced into the surface 84 of the bone 80 to prevent the distal end 26 of the needle 20 from moving laterally along the surface 84 of the bone 82 during the procedure. Alternatively, if the distal end 26 of the needle 20 is only beveled or pointed (as shown in FIGS. 1A–2B), the distal tip 27 may be forced into the surface 84 of the bone 82 to minimize lateral movement. In addition or alternatively, the handle 12 may be held stationary by the user or by an external support device (not shown) to prevent substantial movement of the distal end 26 of the needle 20 relative to the bone 82.

Turning to FIG. 4B, the bit 33 of the drill 30 may be extended from the lumen 28 and advanced into the bone 82. Preferably, the pointed tip 36 of the drill 30 may initially bite into the surface 84 of the bone 82 until the thread pattern 34 begins to engage the bone 82, whereupon the drill 30 may be rotated to advance the distal end 33 into the bone 82. The drill 30 may be rotated and/or advanced manually, e.g., by manipulating an actuator, such as the knob 42 shown in FIGS. 1A and 1B or the trigger 140 shown in FIG. 5. Alternatively, the drill 30 may be coupled to a driver, such as the external driver 50 or internal motor 52 shown in FIG. 3, that may rotate and/or advance the drill 30 relative to the needle 20. The driver may simultaneously advance and rotate the bit 33 at rotational and axial rates that are predetermined relative to one another to minimize stripping or otherwise damaging the bone 82, as will be appreciated by those skilled in the art.

Returning to FIG. 4B, once the bit 33 of the drill 30 reaches the target region 80, optionally, the drill 30 may be locked to prevent retraction into the needle 20. Energy may be delivered to the electrically conductive region 32 of the bit 33 from an energy source (not shown, see, e.g., FIG. 3) to ablate or otherwise treat the target region 80. Preferably, the energy source is an RF generator (not shown) that may be used in a monopolar mode. For example, the conductive region 32 of the drill 30 may be coupled to one terminal of the RF generator, and a dispersive electrode (not shown) may be coupled to the other terminal of the RF generator. The dispersive electrode, e.g., an external pad, may be secured to the patient, e.g., to the patient's skin, such that an electrical circuit is created from the conductive region 32 of the bit 33 through the intervening tissue to the dispersive electrode, as is known to those skilled in the art.

Alternatively, it may be possible to operate the apparatus 10 in a bipolar mode, e.g., by providing an electrode (not shown) on the apparatus 10 that is disposed away from the bit 33. For example, an electrode (not shown) may be provided elsewhere on the drill 30 or on the needle 20 adjacent the distal tip 27, i.e., a predetermined distance away from the deployed bit 33. The electrically conductive region 32 of the bit 33 and the electrode (not shown) may be coupled to opposite terminals of an RF generator and operated as is well known to those skilled in the art.

Optionally, as explained above, the bit 33 and/or the distal end 26 of the needle 20 may include a temperature sensor, e.g., a thermocouple or thermister (not shown) for monitoring the temperature of the surrounding tissue as energy is delivered. Thus, power of the energy delivered may be adjusted to maintain a desired temperature sufficient to destroy tissue within the target region 80 without substantially injuring tissue outside the target region 80.

Once the tissue with the target region 80 is destroyed or otherwise treated, energy delivery may be discontinued. The bit 33 may be withdrawn from the target region 80, e.g., by rotating the drill 30 in a direction opposite to the direction used to advance the bit 33. Once the drill 30 is withdrawn into the needle 20 or otherwise withdrawn from the bone 82, the needle 20 may be withdrawn from the patient. If necessary, the tract formed by the drill 30 and/or the needle 20 may be closed using conventional procedures. For example, energy may be delivered to the bit 33 as the needle 20 is withdrawn to heat the surrounding tissue to coagulate or otherwise seal the tract.

In alternative embodiments, e.g., as shown in FIGS. 6A and 6B, a drill may be provided that includes a detachable bit, thereby eliminating the need to withdraw the bit from the target region (not shown). For example, the bit and the distal end of the shaft may include cooperating elements that may selectively detach the bit from the shaft during or after a procedure. When the bit is detachable, it should be formed from materials that are biocompatible such that the bit may remain within the body indefinitely.

In one embodiment, shown in FIG. 6A, the bit 33' and the distal end of the shaft 31' include mating threads 70,' 72.' For example, as shown, the shaft 31' includes a threaded hub 74' and the bit 33' may include a complementary threaded bore 76' having the threads 70,' 72.' Alternatively, the bit 33' may include a threaded hub and the shaft 31' may include a threaded bore (not shown), or the drill 30' may include other mating thread arrangements. Preferably, the threads 70,' 72' are wound such that, when the shaft 31' is rotated in a first direction, the bit 33' is threaded onto the hub 74.' When the bit 33' is advanced from a needle (not shown), e.g., to thread the bit 33' into bone, the shaft 31' may be rotated in the first direction to retain the bit 33' on the hub 74' while simultaneously boring into the bone with the thread pattern 34' facilitating advancing the bit 33' into the bone, similar to the embodiments described elsewhere herein. Once a target region is reached and/or treated, the shaft 31' may be rotated in an opposite direction, thereby unthreading the bit 33' from the hub 74.' Thus, the bit 33' may be detached and implanted at the target region. If the entire bit 33' and/or shaft 31' are not electrically conductive, the bit 33' and/or shaft 31' may include conductive regions and the like (not shown) that contact one another when the bit 33' is attached to the shaft 31.' Thus, electrical energy may be transferred from the shaft 31' to the bit 33' in order to destroy or otherwise treat tissue at the target region, as described previously.

In another embodiment, shown in FIG. 6B, the bit 33" may be connected to the shaft 31" by an electrolytic joint, e.g., thin region 78," to selectively detach the bit 33" from the shaft 31." Once the bit 33" is introduced into a target region and treated, electrical energy may be delivered to the electrolytic joint to melt the joint and release the bit 33" from the shaft 31" as is known in the art. The shaft 31" may then be removed, leaving the bit 33" in place. In further alternatives, cooperating mechanical connectors (not shown) may be provided on the shaft and/or bit that may securely mount the bit to the shaft, yet may be actuated to release the bit from the shaft.

Figure 5:
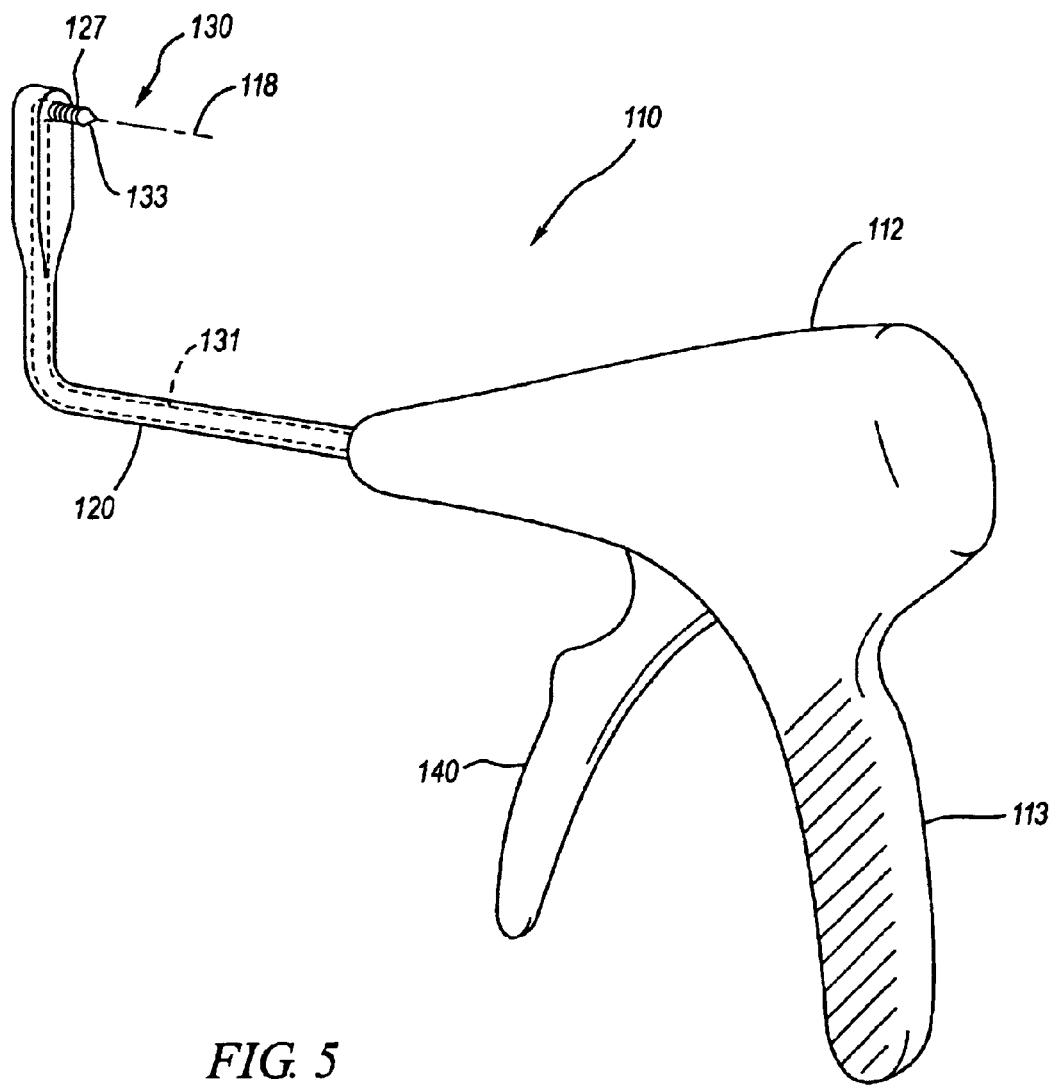
FIG. 5 is a perspective view of an alternative embodiment of an apparatus for treating tissue within a hard tissue structure, including a drill retracted into and deployed from a needle, respectively, in accordance with the present invention.

Turning to FIG. 5, another embodiment of an apparatus 110 is shown that includes similar components as the apparatus 10 described above. Unlike the previous embodiment, the apparatus 110 includes an outer tube 120 with a blunt distal tip 127, although, alternatively, the outer tube 120 may be a needle including a tissue-piercing distal tip (not shown). The outer tube 120 also includes one or more bends, e.g., two bends, as shown. A drill 130 is provided within the outer tube 120 that includes a drive shaft 131 (shown in phantom) and a bit 133. The drill 130 may be rotated about axis 118 and/or advanced and retracted axially relative to the outer tube 120 to deploy or retract bit 133, similar to the previous embodiment. The drive shaft 131 may be axially substantially incompressible such that an axial force on the drive shaft 131 transfers substantially to the bit 133. In addition, the drive shaft 131 may be transversely flexible such that the drive shaft 131 may move around bends within the outer tube 120. Finally, the drive shaft 131 may also be torsional substantially rigid such that rotation of drive shaft 131 about the axis 118 transfer substantially to the bit 133.

In addition, the apparatus 110 includes a handle 112 that includes a stationary grip 113 and a trigger 140. The trigger 140 may be coupled to an internal mechanical drive (not shown) within the handle 112 that may be coupled to the drive shaft 131. During use, the grip 113 may be held to manipulate the apparatus 110, e.g., to advance the outer tube 120 towards a target tissue region. The trigger 140 may be pulled relative to the stationary grip 113, thereby advancing the bit 133 from the distal end 127 of the outer tube 120 and/or rotating the bit 133, similar to the previous embodiment. Exemplary trigger handles and mechanical drives are disclosed in U.S. Pat. Nos. 5,611,515, 5,860,425, 5,842,478, and 5,836,314, the disclosures of which are expressly incorporated by reference herein.

During use, the outer tube 120 may be advanced through a body passage within a patient (not shown) until the distal tip 127 is disposed adjacent a target tissue region, a bone (also not shown). Alternatively, if the outer tube 120 is replaced with a sharpened needle (not shown), the needle may be introduced percutaneously and advanced through tissue until the distal tip 127 is adjacent a target tissue region. The distal tip 127 may be disposed adjacent the target region (or penetrated at least partially into the target region if a sharpened distal tip is provided, similar to the previous embodiment).

Once the target region is accessed, the trigger 140 may be pulled to advance and/or rotate the bit 133 into the target region. Energy may be delivered via an electrode and/or conductive region on the bit 133 to ablate tissue within the target region. Once the treatment is complete, the apparatus 110 may be removed, similar to the previous embodiment.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for delivering energy to a target site within a patient, comprising:
   a handle comprising a proximal end and a distal end;
   an elongated needle extending from the distal end of the handle and terminating in a tissue piercing distal tip, the needle comprising a lumen therein extending from the distal tip towards the handle; and
   a drill disposed within the lumen and extendable from the distal tip of the needle, the drill comprising a tissue boring element and a therapeutic tissue ablative element.

2. The apparatus of claim 1, wherein the distal tip the needle comprises an engaging tip for securing the needle relative to surface of a hard tissue structure within patient's body.

3. The apparatus of claim 1, wherein the distal tip of the needle comprises a serrated edge.

4. The apparatus of claim 1, wherein the tissue boring element is configured for boring a hole in a hard tissues structure.

5. The apparatus of claim 1, wherein the tissue boring element comprises a helical thread pattern extending along the drill.

6. The apparatus of claim 1, wherein the drill comprises a shaft and a bit carrying the tissue boring element and tissue ablative element, and wherein the bit is selectively detachable from the shaft via actuation solely at a proximal end of the shaft.

7. The apparatus of claim 6, wherein the bit is selectively detachable from the shaft by at least one of mating threads, an electrolytic joint, and a mechanical connector.

8. The apparatus of claim 1, further comprising a driver coupled to the drill for rotating the drill about a longitudinal axis of the needle.

9. The apparatus of claim 8, wherein the driver comprises a motor located inside the handle.

10. The apparatus of claim 8, wherein the driver comprises a mechanical drive, and wherein the handle comprises a trigger coupled to the mechanical drive for rotating the drill when the trigger is manipulated.

11. The apparatus of claim 8, wherein the driver is configured for advancing the drill axially as the drill is rotated.

12. The apparatus of claim 8, wherein the driver comprises an external motor coupled to a drill shaft extending through the handle and needle to the drill.

13. The apparatus of claim 1, further comprising an energy source coupled to the drill for delivering therapeutic ablation energy to the tissue ablative element.

14. The apparatus of claim 13, wherein the energy source comprises a radio frequency electrical energy generator.

15. The apparatus of claim 1, further comprising an actuator on the handle coupled to the drill such that axial positioning of the drill relative to the distal tip of the needle is controllable by manipulating the actuator.

16. The apparatus of claim 15, wherein the actuator comprises a lock that selectively prevents the drill from moving axially relative to the distal tip of the needle.

17. The apparatus of claim 1, wherein the tissue ablative element comprises an electrode.

18. The apparatus of claim 1, wherein the needle is detachable from the distal end of the handle.

19. The apparatus of claim 18, wherein the drill is detachable from the handle.

20. The apparatus of claim 1, wherein the needle is substantially rigid.

21. The apparatus of claim 20, wherein the needle comprises one or more bends between the distal end of the handle and the distal tip.

22. The apparatus of claim 20, wherein the drill comprises a drive shaft disposed within the needle.

23. The apparatus of claim 22, wherein the drive shaft is sufficiently flexible to accommodate advancement around the one or more bends.

24. An apparatus for delivering energy to a target site within a patient, comprising:

a handle comprising a proximal end and a distal end;

an elongated needle extending from the distal end of the handle thereby defining a longitudinal axis, the needle comprising a lumen therein extending to a tissue piercing distal tip of the needle;

a drill disposed within the lumen and comprising a bit that is extendable from the distal tip of the needle, the bit comprising a therapeutic tissue ablative element and a tissue boring element;

a driver coupled to the drill for rotating the tissue boring element about the longitudinal axis; and an energy source coupled to the drill for delivering therapeutic ablation energy to the tissue ablative element.

25. The apparatus of claim 24, further comprising an actuator coupled to the drill such that axial positioning of the bit relative to the distal tip of the needle is controllable by manipulating the actuator.

26. The apparatus of claim 25, wherein the actuator comprises a lock that selectively prevents the drill from moving axially relative to the distal tip of the needle.

27. The apparatus of claim 24, wherein the distal tip of the needle comprises a serrated edge.

28. The apparatus of claim 24, wherein the tissue boring element is configured for boring a hole in a hard tissue structure.

29. The apparatus of claim 24, wherein the energy source comprises a radio frequency electrical energy generator.

30. The apparatus of claim 24, wherein the driver comprises a motor located inside the apparatus.

31. The apparatus of claim 24, wherein the driver comprises a mechanical drive, and wherein the handle comprises a trigger coupled to the mechanical drive for rotating the drill when the trigger is manipulated.

32. The apparatus of claim 24, wherein the tissue ablative element comprises an electrode.

33. The apparatus of claim 24, wherein the needle is detachable from the distal end of the handle.

34. The apparatus of claim 33, wherein the drill is detachable from the handle.

35. The apparatus of claim 24, wherein the needle is substantially rigid.

36. The apparatus of claim 35, wherein the needle comprises one or more bends between the distal end of the handle and the distal tip.

37. The apparatus of claim 36, wherein the drill comprise a drive shaft disposed within the needle, the drive shaft being sufficiently flexible to accommodate advancement around the one or more bends.

38. The apparatus of claim 24, wherein the drill comprises a shaft, and wherein the bit is selectively detachable from the shaft via actuation solely at a proximal end of the shaft.

39. The apparatus of claim 38, wherein the bit is selectively detachable from the shaft by at least one of mating threads, an electrolytic joint, and mechanical connector.

* * * * *